United States Patent
Nabutovsky et al.

(10) Patent No.: US 7,725,187 B1
(45) Date of Patent: *May 25, 2010

(54) MOTION DETECTION FOR SENSORS SENSITIVE TO MOTION INDUCED NOISE

(75) Inventors: Yelena Nabutovsky, Mountain View, CA (US); Taraneh Ghaffari Farazi, San Jose, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 734 days.

This patent is subject to a terminal disclaimer.

(21) Appl. No.: 11/556,905

(22) Filed: Nov. 6, 2006

(51) Int. Cl.
*A61N 1/08* (2006.01)

(52) U.S. Cl. ...................................................... 607/19
(58) Field of Classification Search .................. 607/19; 600/510, 515
See application file for complete search history.

(56) References Cited

U.S. PATENT DOCUMENTS

| | | | |
|---|---|---|---|
| 5,766,227 A | 6/1998 | Nappholz et al. | |
| 6,321,115 B1 | 11/2001 | Mouchawar et al. | |
| 6,408,198 B1 | 6/2002 | Hanna et al. | |
| 6,699,199 B2 | 3/2004 | Asada et al. | |
| 6,905,470 B2 | 6/2005 | Lee et al. | |
| 6,997,879 B1 | 2/2006 | Turcott | |
| 7,020,507 B2 | 3/2006 | Scharf et al. | |
| 7,403,813 B1 * | 7/2008 | Farazi et al. | 600/515 |
| 7,447,540 B1 * | 11/2008 | Nabutovsky et al. | 600/510 |
| 2003/0083713 A1 | 5/2003 | Palreddy et al. | |
| 2004/0019289 A1 * | 1/2004 | Ross | 600/519 |
| 2005/0165316 A1 | 7/2005 | Lowery et al. | |

* cited by examiner

*Primary Examiner*—Mark W Bockelman
*Assistant Examiner*—Eric D. Bertram
(74) *Attorney, Agent, or Firm*—Theresa A. Takeuchi; Steven M. Mitchell

(57) ABSTRACT

Provided herein are implantable systems, and methods for use therewith, for estimating a level of noise in a signal produced by an implantable sensor that is sensitive to motion induced noise. Sample data is obtained that is representative of a window of a signal produced by the implantable sensor that is sensitive to motion induced noise. Such sample data includes a plurality of samples each having a magnitude (e.g., amplitude). Each of at least some of the samples is assigned to one of a plurality of bins based on the magnitude of the sample, wherein each bin corresponds to a different range of magnitudes. The plurality of bins includes at least a low bin defining a lowest magnitude range and a high bin defining a highest magnitude range. A level of motion induced noise in the sensor signal is estimated based on a distribution of the samples to the bins.

22 Claims, 10 Drawing Sheets

MOTION DETECTION FOR SENSORS SENSITIVE TO MOTION INDUCED NOISE

CROSS-REFERENCE TO RELATED APPLICATIONS

The present application relates to the following commonly assigned patent applications, each of which is incorporated herein by reference: U.S. Pat. No. 7,403,813, entitled "Systems and Methods for Detection of VT and VF from Remote Sensing Electrodes", issued Jul. 22, 2008; U.S. Pat. No. 7,447,540, issued Nov. 4, 2008, entitled "Systems and Methods for Detection of VT and VF from Remote Sensing Electrodes"; and U.S. patent application Ser. No. 11/556,911, filed the same day as the present application, entitled "Morphology Based Motion Detection for Sensors Sensitive to Motion Induced Noise".

FIELD OF THE INVENTION

Embodiments of present invention relate to estimating levels of motion induced noise in signals produced by sensors that are sensitive to motion induced noise, as well as to making determinations based on such estimated levels of motion induced noise.

BACKGROUND

Some implantable sensors are highly sensitive to motion artifacts, which are otherwise referred to herein as motion induced noise. An example of such a sensor is a photoplethysmography (PPG) sensor. A PPG sensor relies on the transmission and reception of light signals to produce a PPG signal that can be used to monitor various parameters, such as, but not limited to, heart rate, respiration rate, arterial pressure, and arterial oxygen saturation levels. A PPG signal can also be used for adjusting pacing parameters such as AV delay and W delay for pacing optimization. Accordingly, it may be useful to implant a PPG sensor within a patient, so that specific parameters can be chronically monitored or adjusted based on a PPG signal. However, it would be undesirable and potentially detrimental to use such a sensor signal when it is corrupted by motion induced noise. For example, where a PPG signal is being used to adjust a pacing parameter, it may be detrimental to use the PPG signal to adjust the pacing parameter when the PPG is corrupted by motion induced noise.

One way to detect when motion is present is to use a separate motion sensor, such as an accelerometer. However, including a motion sensor can add to the cost and complexity of an implantable system. Further, even if an implantable system already includes a motion sensor, it would add to the complexity of the system to require that the output of the motion sensor be used to make decisions with respect to another sensor that is not specifically intended to detect motion but which is nevertheless sensitive to motion induced noise. Accordingly, it would be useful to provide new ways for determining levels of motion induced noise in signals produced by sensors (e.g., PPG sensors) that are sensitive to such noise.

SUMMARY

Embodiments of the present invention are directed to implantable systems, and methods for use therewith, that estimate a level of noise in a signal produced by an implantable sensor that is sensitive to motion induced noise. In accordance with specific embodiments, the implantable sensor is an implantable photoplethysmograpy (PPG) sensor that produces a photoplethysmography (PPG) signal, which can be used, e.g., for pulse oximetry. However, embodiments of the present invention are also useful with other sensors that produce signals that are sensitive to motion induced noise, such as, but not limited to, glucose sensors, pressure sensors, temperature sensors, sound sensors (e.g., microphones), impedance sensors, venous oxygen sensors, etc.

In accordance with specific embodiments, sample data is obtained that is representative of a window of a signal produced by the implantable sensor that is sensitive to motion induced noise. Such sample data includes a plurality of samples each having a magnitude (e.g., amplitude). Each of at least some of the samples is assigned to one of a plurality of bins based on the magnitude of the sample, wherein each bin corresponds to a different range of magnitudes. The plurality of bins includes at least a low bin defining a lowest magnitude range and a high bin defining a highest magnitude range. A level of motion induced noise in the sensor signal is estimated based on a distribution of the samples to the bins.

In certain embodiments, there is a determination of a ratio of a number of samples in the highest N bins to a number of samples in the lowest M bins, or vice versa, where N and M are integers $\geq 1$, and N+M$\leq$a total number of the bins. In accordance with embodiments, the determined ratio can be used as a reliability index indicative of the reliability of the sensor signal (or sample data thereof). In accordance with embodiments, the determined ratio can be compared to one or more threshold to estimate the level of motion induced noise. For example, the ratio can be compared to one threshold to classify the level of motion induced noise as low or high. If two thresholds are used, the level of motion induced noise can be classified as low, medium or high. More generally, the determined ratio can be compared to N thresholds, to estimate the level of motion induced noise in the sensor signal as being one of N+1 levels, where N is an integer that is $\geq 1$.

In other embodiments, a line is fit to the distribution of the samples to the bins, and a slope of the line is determined. In such embodiments, a level of motion induced noise can be estimated based on the slope of the line. Generally, the determined slope of the line can be compared to N thresholds, to estimate the level of motion induced noise in the sensor signal as being one of N+1 levels, where N is an integer that is $\geq 1$.

The sensor signal produced by the implantable sensor may be used by an implantable system to monitor or adjust one or more parameter. Where that is the case, there can be a determination, based on the estimated level of noise, of whether to use the sensor signal (or sample data thereof) to monitor or adjust the parameter(s).

Specific embodiments of the present invention also relate to updating threshold(s) and/or a boundaries of bins to compensate for changes in the performance of an implantable sensor, which may occur over time due to electrical depletion of the sensor and/or the battery that powers the sensor, tissue overgrowth and/or other factors.

In accordance with specific embodiments, sample data is obtained that is representative of a signal produced by the implantable sensor that is sensitive to motion induced noise. Such a sensor signal has a corresponding morphology. In accordance with embodiments, the morphology of a portion of the sensor signal is compared to a template, and a level of motion induced noise in the sensor signal is estimated, based on results of the morphology comparison. Such embodiments rely on the principle that noise due to motion will have a different morphology than the actual sensor signal. These embodiments, as will be appreciated from the description below, work best with sensor signals that have a distinct morphology.

In certain embodiments, there is a determination of a level of similarity between the morphology of the portion of the sensor signal and the template, and the level of motion induced noise in the sensor signal is estimated based on the level of similarity. The level of similarity can be determined in a variety of manners, including the use of correlation or an established morphology algorithm. In a specific implementation, the portion of the sensor signal is aligned with the template, areas under the curve of the sensor signal and under the curve of the template are determined, and difference between the determined areas under the curves is determined. The level of similarity can then be determined based on the difference in areas under the curves.

In accordance with embodiments, the determined level of similarity can be used as a reliability index indicative of the reliability of the sensor signal. In accordance with embodiments, the determined level of similarity can be compared to one or more threshold to estimate the level of motion induced noise. For example, the level of similarity can be compared to one threshold to classify the level of motion induced noise as low or high. If two thresholds are used, the level of motioned induced noise can be classified as low, medium or high. More generally, the determined level of similarity can be compared to N thresholds, to estimate the level of motion induced noise in the sensor signal as being one of N+1 levels, where N is an integer that is $\geq 1$.

The sensor signal produced by the implantable sensor may be used by an implantable system to monitor or adjust one or more parameter. Where that is the case, there can be a determination, based on the estimated level of noise (or level of similarity), of whether to use the sensor signal to monitor or adjust the parameter(s).

Specific embodiments of the present invention also take into account that certain sensor signals may experience a morphology reversal, e.g., along a vertical axis. To check for this case, a level of similarity can be determined between the morphology of the portion of the sensor signal and a reversed template. Alternatively, the sample data for the portion of the sensor signal can be reversed and compared to the normal template.

Specific embodiments of the present invention also relate to updating the template to compensate for changes in the performance of an implantable sensor, which may occur over time due to electrical depletion of the sensor and/or the battery that powers the sensor, tissue overgrowth and/or other factors.

This description is not intended to be a complete description of, or limit the scope of, the invention. Other features, aspects, and objects of the invention can be obtained from a review of the specification, the figures, and the claims.

DETAILED DESCRIPTION

Figure 1:
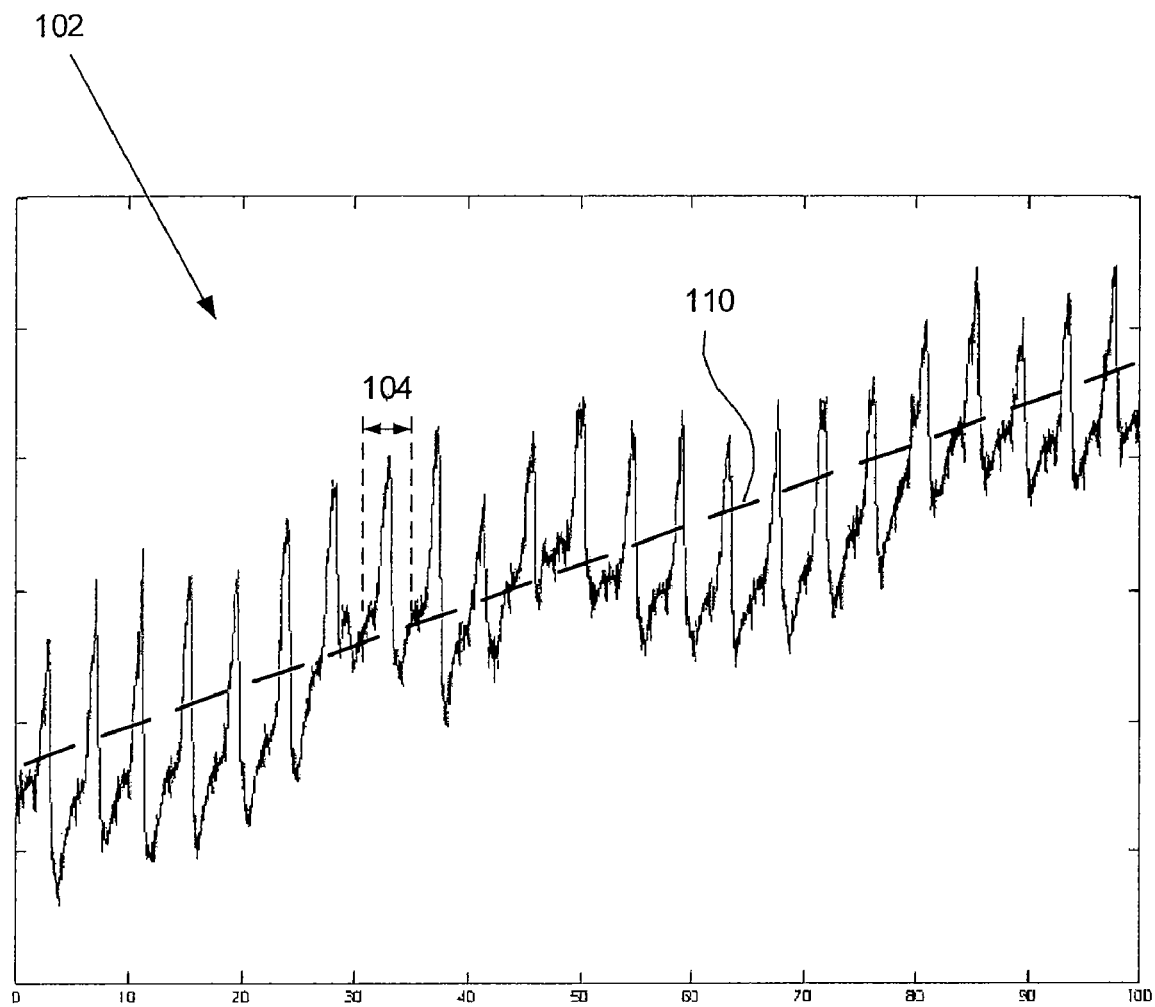
FIG. 1 is an exemplary graph of a PPG signal that is generally unaffected by motion induced noise.

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit(s) of a reference number identifies the drawing in which the reference number first appears.

As mentioned above, a photoplethysmography (PPG) sensor is an example of a sensor that is highly sensitive to motion induced noise. To help understand why this is the case, details of an exemplary PPG sensor are described below.

A PPG sensor typically includes a light source and a light detector. The light source can include, e.g., one or more light-emitting diode (LED), incandescent lamp or a laser diode, outputs a transmit light signal that is transmitted through and/or reflected by patient tissue. A receive light signal is received by the light detector, which can include, e.g., a photoresistor excited by a constant current source. Changes in light intensity cause proportional changes in the resistance of the photoresistor. Since the current through the photoresistor is constant in this example, the resistance changes produce a varying analog voltage light detection signal. This varying analog voltage light detection signal, which is a photoplethysmography (PPG) signal, is typically filtered and amplified and then converted to a digital signal using an analog to digital converter. The light detector, which can also be referred to as a photodetector or photocell, can alternatively include a photodiode, phototransistor, photodarlington or avalanche photodiode.

PPG sensors may operate in either a transmission configuration or a reflection configuration. In the transmission configuration, the light source and the light detector face one another with patient tissue interposed between the source and the detector. In the reflection configuration, the light source and the light detector are mounted adjacent to one another. In this configuration, a fraction of light from the light source is backscattered by the tissue into the light detector.

When the PPG sensor is implanted and/or incorporated into a chronically implantable device (e.g., an implantable cardioverter defibrillator (ICD), pacemaker, or any other implantable device), the light source and the light detector can be mounted adjacent to one another on the housing or header of the implantable device, or in a separate housing that is attached to a primary housing. The light source and light detector can alternatively be within or attached to a lead that is attached to an implanted housing. For example, the light source and the light detector can be placed on the side of an implantable device that, following implantation, faces the chest wall, and be configured such that light cannot pass directly from the source to the detector (resulting in a reflection configuration). Alternatively, at the risk of increasing susceptibility to ambient light, the light source and the light detector can be placed on the side of the device that faces the skin of the patient.

Voluntary movement by a patient, such as walking, twisting, moving a limb, or the like, can affect the tissue through which light is transmitted and/or off which light is reflected, thereby affecting the intensity of light received by the light detector. Additionally, involuntary muscle movement can affect the intensity of the light received by the light detector. Further, movement of a patient's surrounding (e.g., if the patient is in a car, airplane or elevator) can effect the intensity of the light received by the light detector. Such are examples of things that can result in motion induced noise in a PPG signal, or any other sensor that produces a signal that is sensitive to motion induced noise.

PPG signals are used by pulse oximetry sensors, which are also known as pulse oximeters, oximetry sensors or oximeter sensors. This is why a PPG sensor is sometimes referred to as a PPG/oximetry sensor. Pulse oximeters combine the principles of photoplethysmography and spectrophotometry to determine arterial oxygen saturation values. Photoplethysmography, as just explained above, uses light absorbance technology to reproduce waveforms produced by pulsating blood. Spectrophotometry uses various wavelengths of light to perform quantitative measurements of light absorption through given substances. Using these two principles, the arterial oxygen saturation of a patient's blood can be estimated. Arterial oxygen saturation measurements can be used, for example, to monitor and assess heart failure, sleep apnea, and pulmonary function.

Conventional multi-wavelength pulse oximeters (which perform pulse oximetry) emit light of two or more wavelength (e.g. from two or more LEDs) into a vascularized tissue bed and collect the transmitted light with a photodetector positioned on an opposite surface (transmission pulse oximetry), or an adjacent surface (reflectance pulse oximetry). The "pulse" in pulse oximetry comes from the time varying amount of arterial blood in the tissue during the cardiac cycle, and the processed signals from the photodetector create the familiar plethysmographic waveform due to the cycling light attenuation. For estimating oxygen saturation, at least one of the LEDs' primary wavelength is chosen at some point in the electromagnetic spectrum where the absorption of oxyhemoglobin (HbO2) differs from the absorption of reduced hemoglobin (Hb). The one or more other wavelengths should be at a different point in the spectrum where, additionally, the absorption differences between Hb and HbO2 are different from those at the first wavelength. Pulse oximeters typically utilize one wavelength in the red part of the visible spectrum near 660 nanometers (nm), and at least one in the near infrared part of the spectrum in the range of 880 nm-940 nm. Photocurrents generated within the photodetector are detected and processed for measuring the ratio of the red to infrared signals. This ratio has been observed to correlate well to arterial oxygen saturation. It is also possible that a single wavelength is used, to not determine a ratio, but rather to measure relative changes in oxygen saturation. Because pulse oximeters (i.e., oximetry sensors) also rely on accurately measuring the intensity of light transmitted through or reflected off of patient tissue, oximetry sensors are very sensitive to motion induced noise.

Exemplary additional details of implantable PPG and oximetry sensors are disclosed in U.S. Pat. No. 6,491,639, entitled "Extravascular Hemodynamic Sensor" (Turcott), which is incorporated herein by reference. Exemplary additional details of PPG and oximetry sensors that are located in a module housing that is attached to an ICD are disclosed in U.S. patent application Ser. No. 10/913,942, filed Aug. 5, 2004, entitled "Autonomous Sensor Modules For Patient Monitoring" which is incorporated herein by reference. Exemplary additional details of PPG and oximetry sensors that are located within an implantable lead that is connected to a chronically implanted device (e.g., an ICD), as disclosed in U.S. patent application Ser. No. 11/231,555, filed Sep. 20, 2005, entitled "Implantable Multi-Wavelength Oximeter Sensor" which is incorporated herein by reference.

As alluded to above, a problem with current methods and devices for performing photoplethysmography and pulse oximetry is that they are acutely sensitive to sensor and/or tissue motion. Even rather subtle motion can (and often does) swamp the detected optical signals and renders the measurements taken therefrom unusable. Embodiments of present invention, which are discussed below, can be used to estimate levels of motion induced noise in signals produced by sensors that are sensitive to noise, such as PPG and oximetry sensors. While much of the following discussion mentions the use of the embodiments of the present invention with implantable PPG sensors, embodiments of the present invention are not limited to uses therewith. Rather, as will be appreciated from the following discussion, embodiments of the present invention can be used with other types of implantable sensors that produce sensor signals that are sensitive to motion induced noise.

FIG. 1 is an exemplary graph of a PPG signal 102 that is generally unaffected by motion induced noise. Each PPG pulse 104 corresponds to a cardiac cycle. As can be appreciated from FIG. 1, the peak-to-peak amplitude of each cycle is relatively similar. However, there are changes to the minimum and maximum amplitudes relative to the y-axis from cycle to cycle, which is due to respiration.

Figure 2:
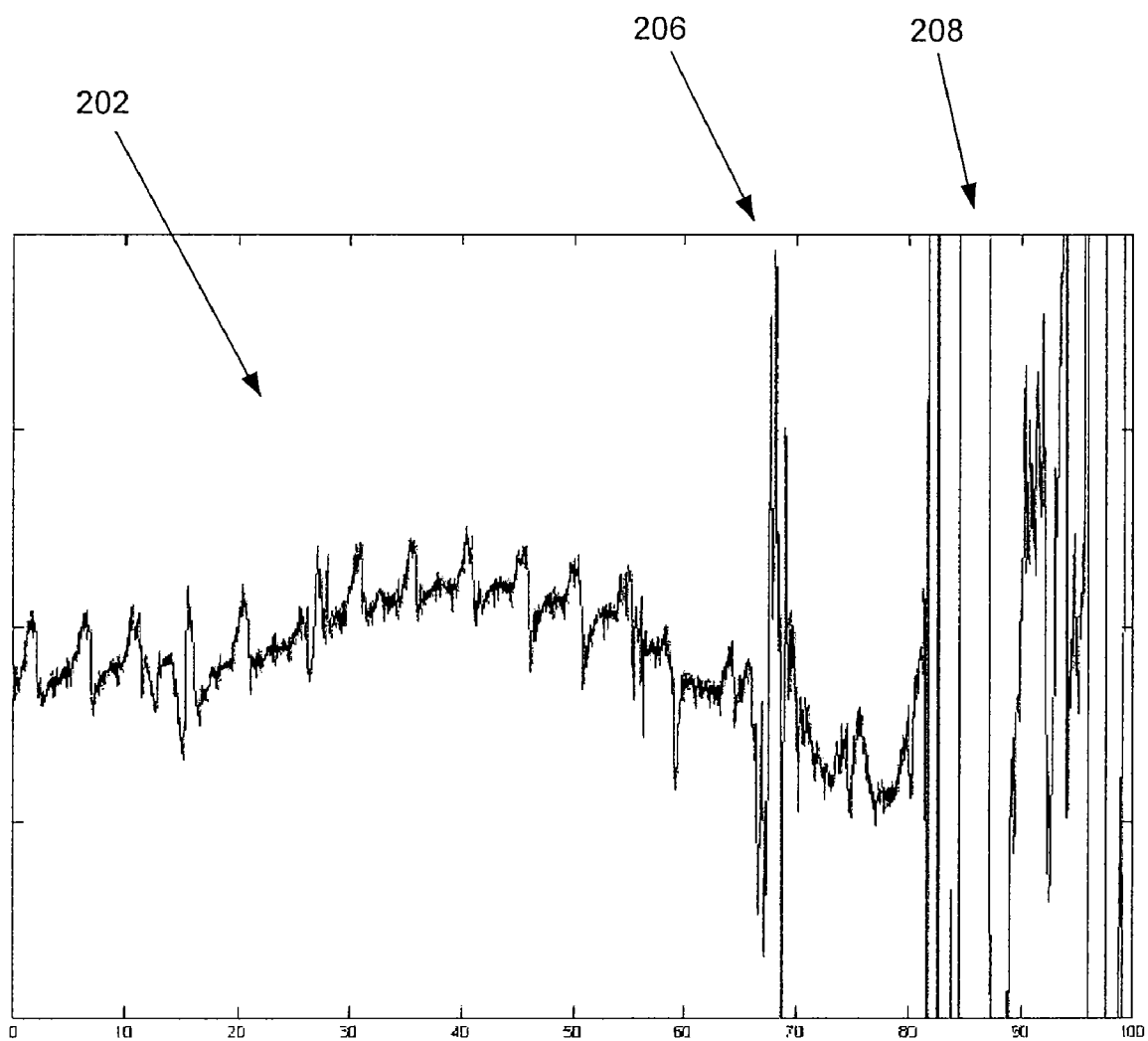
FIG. 2 is an exemplary graph of a PPG signal that is initially generally unaffected by motion induced noise, but becomes swamped by motion induced noise.

FIG. 2 is an exemplary graph of a PPG signal 202 that is initially generally unaffected by motion induced noise, but that at periods 206 and 208 is swamped by motion induced noise. As can be appreciated from FIG. 2, the motion induced noise renders sensor signal 202 generally meaningless during periods 206 and 208.

Embodiments of the present invention, as will be described below, monitor the sensor signal itself to determine whether the signal has been corrupted by motion induced noise. Optionally, the sensor signal (or sample data thereof) is high pass filtered or band pass filtered prior to such determination, to get rid of frequency components which are known to not be of interest. The signal and/or sample data may also be normalized, detrended and/or rectified, as will be described below.

Histogram Techniques

Figure 3:
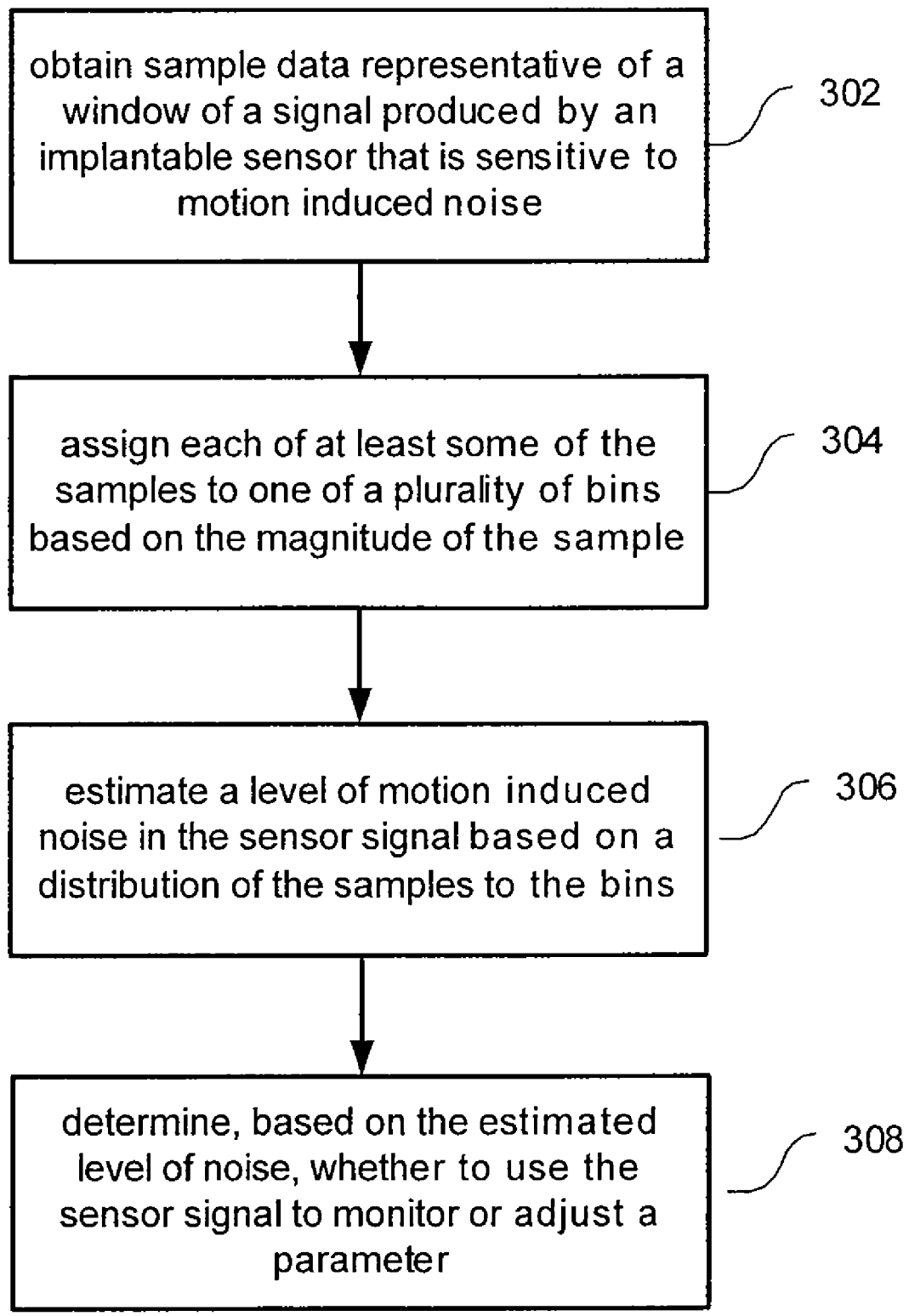
FIG. 3 is a high level flow diagram that is useful for describing specific embodiments of the present invention, for estimating a level of motion induced noise in a signal produced by an implantable sensor that is sensitive to motion induced noise.

FIG. 3 is a high level flow diagram that is useful for describing specific embodiments of the present invention, for estimating a level of motion induced noise in a signal produced by an implantable sensor that is sensitive to motion induced noise. Referring to FIG. 3, at a step 302, sample data is obtained that is representative of a window of a signal produced by an implantable sensor that is sensitive to motion induced noise. Such sample data includes a plurality of samples each having a magnitude (e.g., amplitude). In accordance with an embodiment, step 302 is performed by obtaining a signal produced by the implantable sensor, and sampling the signal to produce a plurality of samples. In specific embodiments, such a signal is a PPG signal obtained from an implanted PPG sensor. However, as explained above, the sensor signal is not limited to this type of signal. Rather, the sensor signal can be any type of signal from a sensor that is sensitive to motion induced noise, such as, but not limited to, glucose sensors, pressure sensors, temperature sensors, sound sensors (e.g., microphones), impedance sensors, venous oxygen sensors, etc.

In accordance with an embodiment, the signal obtained from the sensor, and/or the samples of the signal, are high pass filtered and/or detrended, so that trends and low frequency events that are not of interest have already been removed from the sample data obtained at step 302. The purpose of the high pass filtering is to remove low frequency components of the signal that are due to respiration or other low frequency events that are not of interest. Band pass filtering, which includes high pass filtering, may also be used. The purpose of the detrending is to remove any constant, linear or piecewise linear trend from the sensor signal (or the samples of the sensor signal). For example, referring back to FIG. 1 it can be seen that the PPG signal has an upward trend within the window of the signal, with dashed line 110 illustrating the trend.

Referring again to FIG. 3, at a step 304, each of at least some of the samples is assigned to one of a plurality of bins based on the magnitude of the sample, wherein each bin corresponds to a different range of magnitudes. For example, there can be ten different bins, including a bin for a lowest range of magnitudes, a bin for a highest range of magnitudes, and eight bins therebetween. In this case, each of the samples can be assigned to one of the ten different bins, based on the magnitude of the sample.

Figure 4:
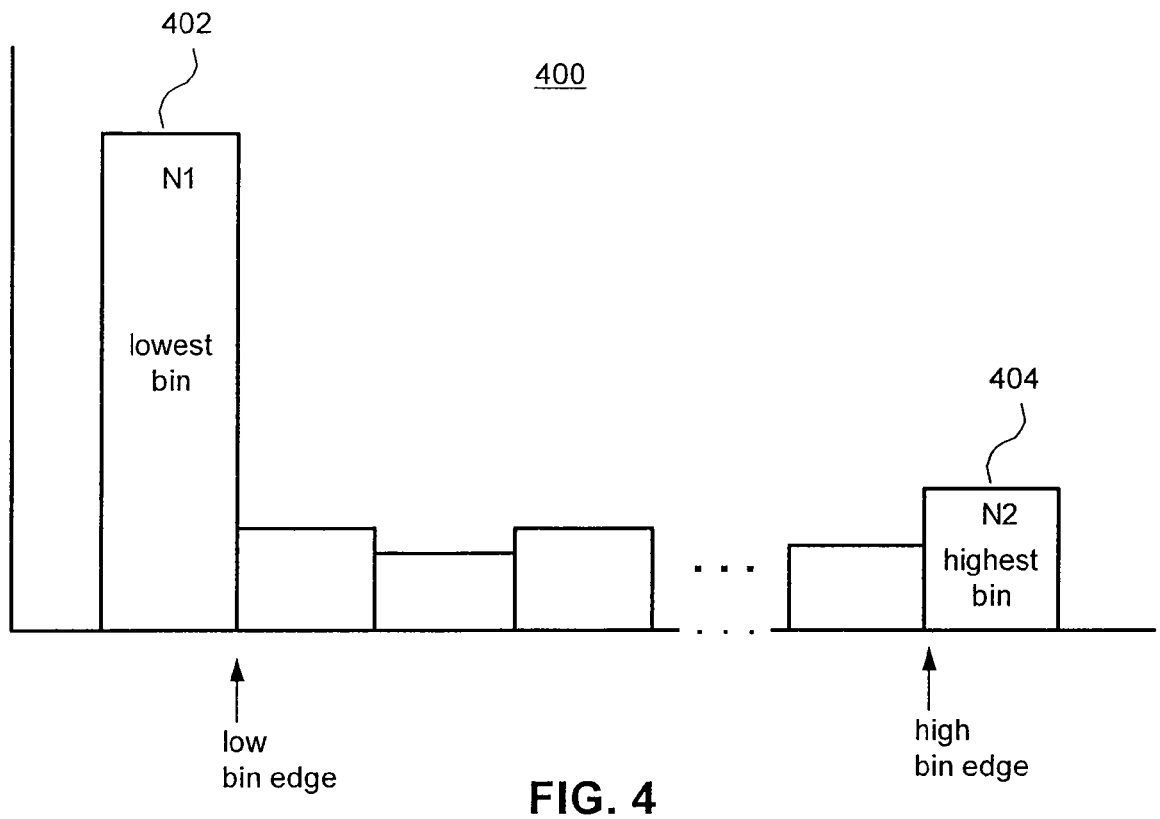
FIG. 4 illustrates an exemplary histogram having a distribution corresponding to a sensor signal having a relatively low level of motion induced noise.
Figure 5:
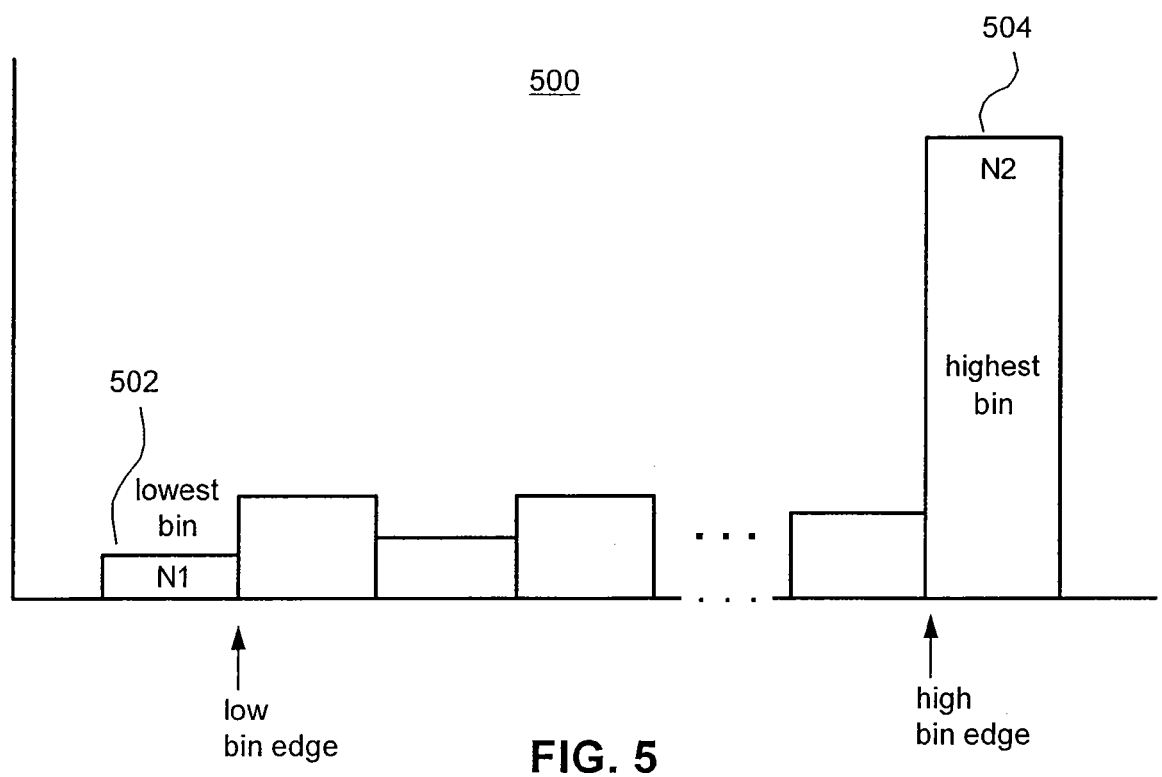
FIG. 5 illustrates an exemplary histogram having a distribution corresponding to a sensor signal having a relatively high level of motion induced noise.

Referring briefly to FIG. 4, an exemplary histogram 400 is shown as including a bin 402 of a lowest range of magnitudes (referred to hereafter as the "lowest bin") and a bin 404 of a highest range of magnitudes (referred to hereafter as the "highest bin"). Such a histogram can be generated at step 304. As can be seen from FIG. 4, there are significantly more samples assigned to the lowest bin 402 than to the highest bin 404, which is indicative of the sensor signal having a relatively low motion induced noise. In contrast, in the exemplary histogram 500 of FIG. 5, there are significantly less samples assigned to the lowest bin 502 than to the highest bin 504, which is indicative of the sensor signal having a relatively high level of motion induced noise.

It is also possible that there are only two bins, including a bin for a lowest range of magnitudes, and a bin for a highest range of magnitudes, with no bins therebetween. In this situation, each of the samples can be assigned to one of these two bins. Alternatively, it is possible that there are only two bins of interest, and that samples not within the range of either of the two bins are discarded. For example, assuming 100 samples, it may be that 25 samples are assigned to a lowest bin, 35 samples are assigned to a highest bin, and that the other 40 samples that are not within the range of either bin are not assigned to either bin. This is why step 304 involves assigning each of at least some of the samples to one of a plurality of bins, because some samples may not be assigned to a bin at all. Each of these variations just described is encompassed by step 304.

The bins and the assigning of samples to bins can be implemented using software, firmware, hardware or combinations thereof. For example, there can be a plurality of counters implemented in software, firmware or hardware (e.g., registers) that act as the bins, with a counter being incremented when the magnitude of a sample is within the range corresponding to the counter. The decisions as to where to assign samples can be performed algorithmically using software or firmware, or hardware type comparators can be used. In a specific embodiment, one or more processor performs all the necessary processing associated with forming the bins and assigning samples to the bins. One of ordinary skill in the art will understand that alternative configurations can be used, while being within the scope of the present invention.

Referring again to FIG. 3, at a step 306, a level of motion induced noise in the sensor signal is estimated based on a distribution of the samples to the bins. As briefly discussed above with reference to FIGS. 4 and 5, it is expected that the lowest bin will have more samples than the highest bin where there is a relatively low level of motion induced noise in the sensor signal, and that the lowest bin will have less samples than the highest bin where there is a relatively high level of motion induced noise in the sensor signal. This can be better understood by referring back to the exemplary PPG sensor signals shown in FIGS. 1 and 2. Referring to FIG. 1, assume that PPG signal 102 is sampled to produce a plurality of samples that are representative of the amplitude of the signal 102, and also assume that the signal 102 or the samples thereof have been high pass filtered and detrended. It can be appreciated that such samples will have a relatively similar magnitude (amplitude in this case). Now referring to FIG. 2, it can be appreciated that samples of the signal 202 during period 208 will have significantly greater magnitude, due to the motion induced noise. Thus, it can be understood how a histogram generated for the signal 102 (or portion thereof) may resemble the histogram 400 shown in FIG. 4, and that a histogram generated for the portion 208 of the signal 202 may resemble the histogram 500 shown in FIG. 5.

In accordance with specific embodiments, step 306 can be accomplished by generating a ratio of the number of samples in the highest bin(s) to the number of samples in the lowest bin(s) (or vice versa), and then estimating the level of motion induced noise based on the ratio. More generally, the ratio can be of a number of samples in the highest N bins to a number of samples in the lowest M bins, or vice versa, wherein N and M are integers $\geq 1$, and N+M$\leq$a total number of the bins. The ratio can then be compared to one or more threshold. For example, if the determined ratio is compared to a single threshold, the level of motion induced noise can be classified as being either low or high. If the ratio is compared to two thresholds, the level of motion induced noise can be classified as being either low, medium or high. Of course more thresholds can be used to classify the level of motion induced noise with more granularity. Generally, where N thresholds are used, the level of motion induced noise can be classified as one of N+1 levels. Such threshold values can be predefined or preprogrammed, or as described below they can be updated from time to time.

Figure 6:
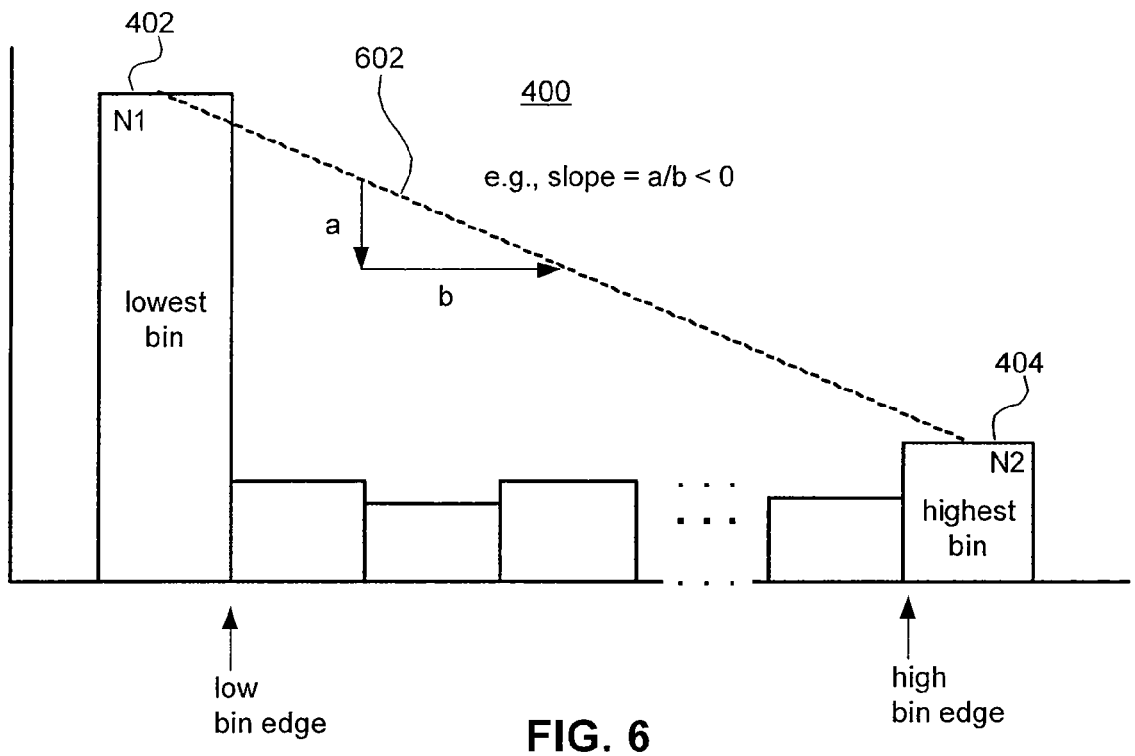
FIG. 6 illustrates how a line can be fit to the histogram of FIG. 4.
Figure 7:
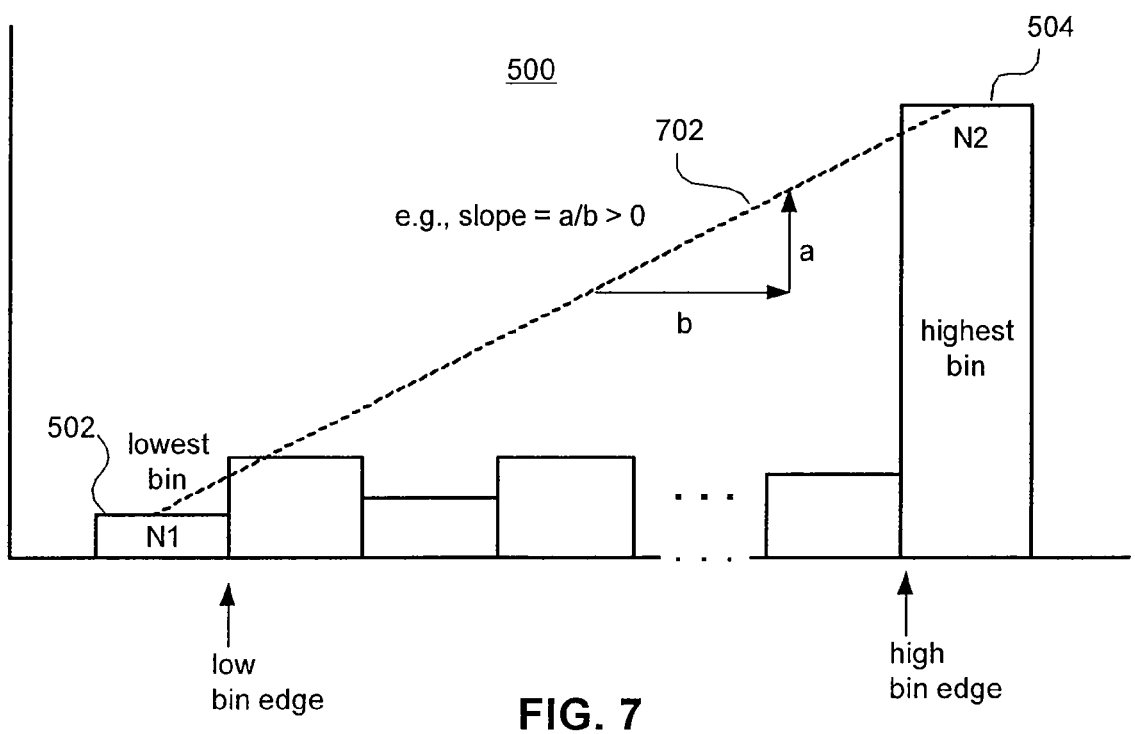
FIG. 7 illustrates how a line can be fit to the histogram of FIG. 5.

In accordance with other embodiments, step 306 can be accomplished by fitting a line to the distribution, determining a slope of the line, and then estimating the level of motion induced noise based on the slope. Examples of this are shown in FIGS. 6 and 7. Referring to FIG. 6, a line 602 is fit to the distribution of histogram 400, which was previously discussed with reference to FIG. 4. As mentioned above, the histogram 400 is representative of a sensor signal with a relative low level of motion induced noise. As can be appreciated from FIG. 6, the line 502 has a negative slope. Referring to FIG. 7, a line 702 is fit to the distribution of histogram 500, which was previously discussed with reference to FIG. 5. As mentioned above, the histogram 500 is representative of a sensor signal with a relatively high level of motion induced noise. As can be appreciated from FIG. 7, the line 702 has a positive slope. The slope can be compared to one or more threshold. For example, if the slope is compared to a single threshold, the level of motion induced noise can be classified as being low or high. For a more specific example, the threshold can be zero, so that if the slope is less than the threshold (i.e., if the slope is negative) then it is estimated that the level of motion induced noise is low, and if the slope is greater than the threshold (i.e., if the slope is positive) then it is estimated that the level of motion induced noise is high. The slope can alternatively be compared to two thresholds, so that the level of motion induced noise can be classified as being either low, medium or high. More thresholds can be used to classify the level of motion induced noise with more granularity. Such threshold values can be predefined or preprogrammed, or as described below they can be updated from time to time.

It is also within the scope of the present invention to use a ratio and/or slope as a reliability index indicative of the reliability of the sensor signal. In this manner, if a sensor signal is deemed to be highly reliable, then a measurement, adjustment, decision or calculation that is based on the sensor signal may be highly weighted. If a sensor signal is deemed to not be reliable, then a measurement, adjustment, decision or calculation based on the sensor signal may be lightly weighted, or disregarded. It may also be that the measurement, adjustment, decision or calculation is not made, when the sensor signal is deemed unreliable.

In certain embodiments, the signal produced by the implantable sensor can be used by the implantable system to monitor a parameter such as, but not limited to, heart rate, respiration rate, atrial or ventricular pressure, arterial or venous oxygen saturation level, level of cardiac output, etc. Alternatively, or additionally, the signal produced by the implantable sensor can be used to adjust a parameter, such as an AV delay or W delay pacing parameter. In such embodiments, there can be a determination, based on the estimated level of noise, of whether to use the sensor signal (or more specifically, the sample data representative of the sensor signal) to monitor or adjust a parameter, as indicated at a step 308 in FIG. 3. For example, if the level of motion induced noise in a signal is classified as being either high or low, it can be that the sample data is only used when the level of motion induced noise is low, but not used when the level of motion induced noise is high. Alternatively, further processing (e.g., further filtering) of the sensor signal (or the samples thereof) can be performed, if the level of motion induced noise is high. Then, before being used, after the sensor signal having a high level of motion induced noise is further processed (e.g., filtered), the signal/samples may again be analyzed to determine whether the level of motion induced noise has been reduced to an acceptable level.

In another example, where the level of motion induced noise is classified as either high, medium, or low, it can be that the signal is used when the level of noise is low, not used when the level of noise is high, and further processed (e.g., filtered) when the noise is medium and thereafter used. Generally, decisions on whether or not to use and/or whether or not to further process a sensor signal can be based on the estimated level of motion induced noise. In other embodiments, determinations of how to weigh sample data, or parameters monitored or adjusted therefrom, can be based on the estimated level of motion induced noise. One of ordinary skill in the art, reading this description, will realize that variations other than those specifically recited above are also within the scope of the present invention.

Generally, what can occur at steps 304 and 306, respectively, is that a histogram is produced based on the plurality of samples, and a level of motion induced noise in the sensor signal is estimated based on a distribution of the histogram. In the manners described above, a ratio and/or slope can be determined based on the histogram, and the level of motion induced noise can be estimated based on the ratio and/or slope.

Since the performance of an implantable sensor may change over time due to electrical depletion of the sensor and/or the battery that powers the sensor, tissue overgrowth and/or other factors, it would be useful to update the parameters that are used to classify the level of motion induced noise from time to time. This can include adjusting the one or more threshold that is used to classify the level of motion induced noise. Alternatively, or additionally, the boundaries of the bins can be adjusted. For example, in accordance with an embodiment, a running average amplitude can be determined for sample data where the level of motion induced noise is determined to be low. This average can then be compared to an average when the thresholds were originally (or last) defined. If the present average is less than the previous average, than the thresholds can be reduced accordingly. Similarly, if the present average is greater than the previous average (when the thresholds were last defined), then the thresholds can be increased accordingly. Alternatively, or additionally, the upper end of the bin for a lowest range of magnitudes (and the lower end of the bin for the highest range of magnitudes) can be lowered accordingly, when the average amplitude decreases. Similarly, the upper end of the bin for a lowest range of magnitudes (and the lower end of the bin for the highest range of magnitudes) can be increased, when the average amplitude increases. Such updating can be performed periodically, e.g., once a week, once a month, etc. Alternatively, the threshold(s) and/or bin boundaries can be updated whenever it is determined that the difference between the running average and the previous average (when the threshold(s)/bin boundaries were last updated) exceeds an update threshold level. Such a comparison can occur generally continuously, or periodically. For example, each time a portion of the sensor signal is determined to have a low level of noise, that portion can be used to update an average of the sensor signal. Each time the average is updated, the updated average can be compared to the average for when the threshold(s) and/or bin boundaries were last updated. Alternatively, such a comparison can occur periodically.

Referring back to FIG. 3, steps 302-308 were described as being performed for a window of a sensor signal. Such a window can be a sliding window, which enables embodiments of the present invention to be performed on a generally continuous basis, by repeating steps 302-308 over time. For example, a sliding window can encompass 400 samples of the sensor signal. The next sliding window can be simply shifted over a single sample, or preferably a more significant distance, such as 50 samples, to avoid almost complete overlap of consecutive sliding windows that are analyzed. It is also possible that consecutive sliding windows do not overlap at all, e.g., consecutive windows of 400 windows can be separated by 50 samples.

Morphology Techniques

Figure 8:
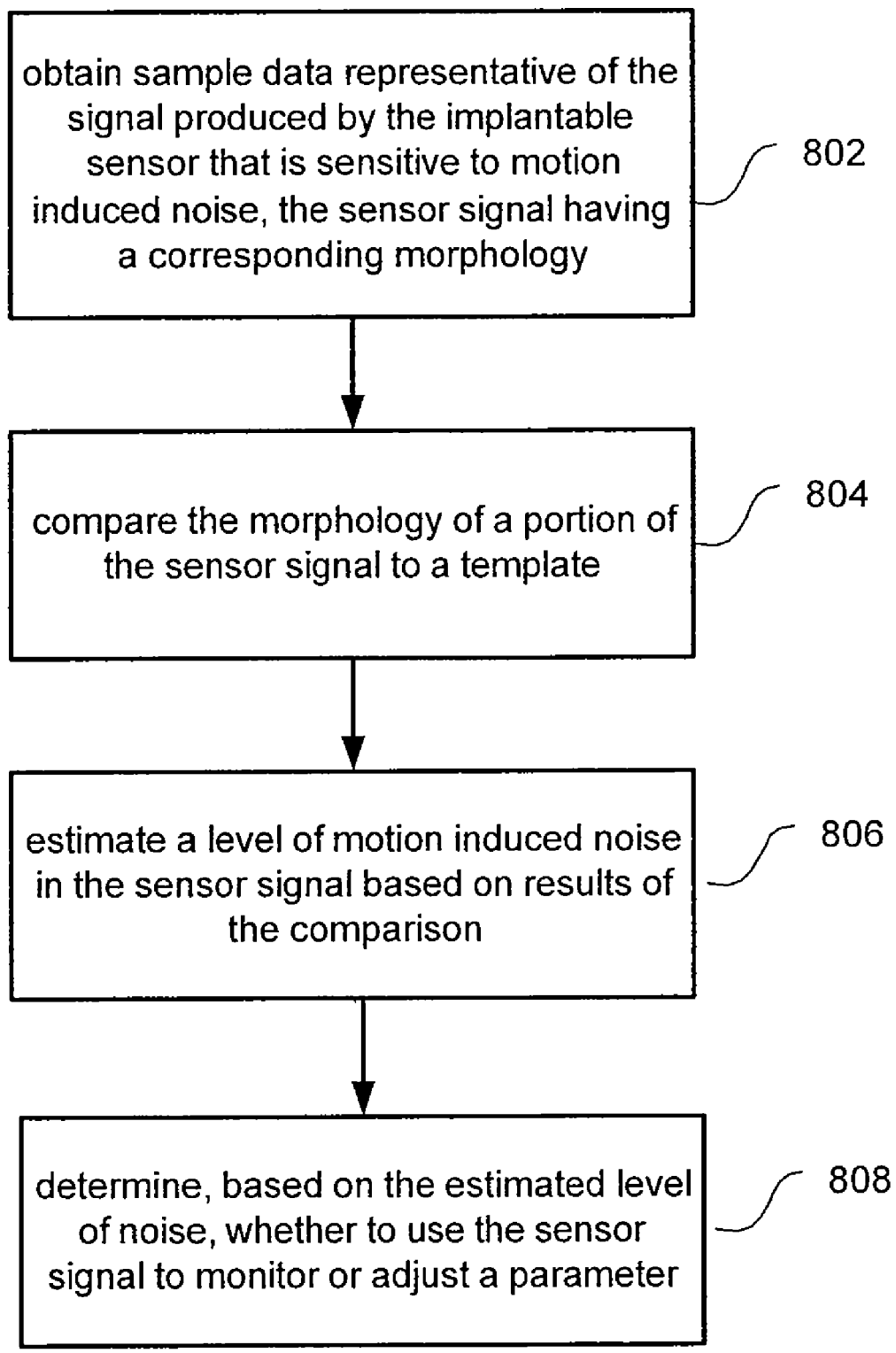
FIG. 8 is a high level flow diagram that is useful for describing alternative embodiments of the present invention, for estimating a level of motion induced noise in a signal produced by an implantable sensor that is sensitive to motion induced noise, based on the morphology of the sensor signal.

FIG. 8 is a high level flow diagram that is useful for describing alternative embodiments of the present invention that are based on the principle that noise due to motion has a different morphology than the actual sensor signal.

Referring to FIG. 8, at a step 802, sample data is obtained that is representative of the signal produced by the implantable sensor that is sensitive to motion induced noise. Because the sensor signal has a corresponding morphology, the sample data includes information about the sensor signal's morphology.

At a step 804, the morphology of a portion of the sensor signal is compared to a template. Such a template morphology can be established, e.g., at an initial implant while the patient is at rest. The template can be based on an average morphology of several cycles of the sensor signal, or simply on a single representative cycle. As will be described below, the template can be updated from time to time (e.g., periodically or aperiodically). Still referring to FIG. 8, at a step 806, a level of motion induced noise in the sensor signal is estimated based on results of the morphology comparison.

In accordance with specific embodiments, at step 804 there is a determination of a level of similarity between the morphology of the portion of the sensor signal and the template. Then, at step 806, the level of motion induced noise is estimated based on the determined level of similarity. In such embodiments, the higher the similarity, the lower the level of motion induced noise, and vice versa (i.e., the lower the similarity, the higher the level of motion induced noise).

The level of similarity between the portion of the sensor signal and the template can be determined in various manners. For example, correlation can be performed to determine a level of similarity. In another embodiment, the portion of the sensor signal can be aligned with the template, and a difference between the area under the curve of the sensor signal and the area under the curve of the template can be determined. In such an embodiment, the lower the difference between areas under the curve, the greater the level of similarity, and vice versa (i.e., the greater the difference between areas under the curve, the lower the level of similarity).

In accordance with embodiments of the present invention, the signal obtained from the sensor, and/or the samples of the sensor signal, are normalized with respect to the template, so that the amplitude (e.g., peak-to-peak) and width of the portion of the signal that is being compared to the template are generally the same as that of the template. For example, if the peak-to-peak amplitude of the portion of a PPG sensor signal ($A_s$) is less than the peak-to-peak amplitude of the template ($A_t$), then the PPG sensor signal (or samples thereof) should be increased in amplitude. This can be accomplished, e.g., by multiplying each sample by $A_t/A_s$. Similarly, if a width of a portion of the sensor signal ($W_s$) representative of one cycle of the sensor signal (e.g., one cycle of a PPG signal) is less than the width of the template cycle ($W_t$), then the sensor signal should be increased in width. Such adjustments in width of the sensor signal (or samples thereof) can be accomplished by adjusting the time resolution of samples, or by adding or removing samples, preferably in an evenly distributed manner. Without such normalization, level of similarity determinations may not be as accurate and useful. Thus, in accordance with preferred embodiments, the sample data obtained at step 802, or the sensor signal from which the sample data is obtained, has already been normalized. It is also within the scope of the present invention that the sample data, or the sensor signal from which the sample data is obtained, has been high pass filtered, rectified and/or detrended.

Figure 9A:
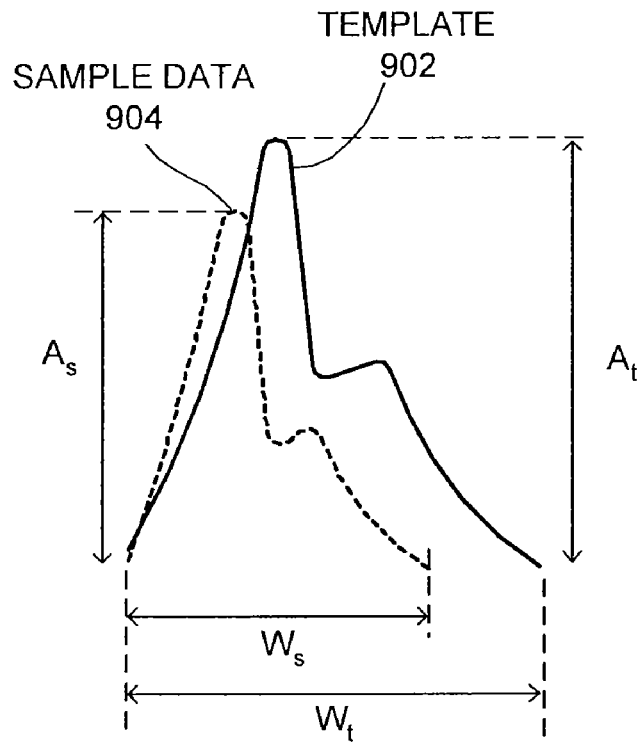
FIGS. 9A and 9B, which illustrate an exemplary portion of a PPG signal as compared to a template, are useful for describing how a portion of a sensor signal can be normalized.
Figure 9B:
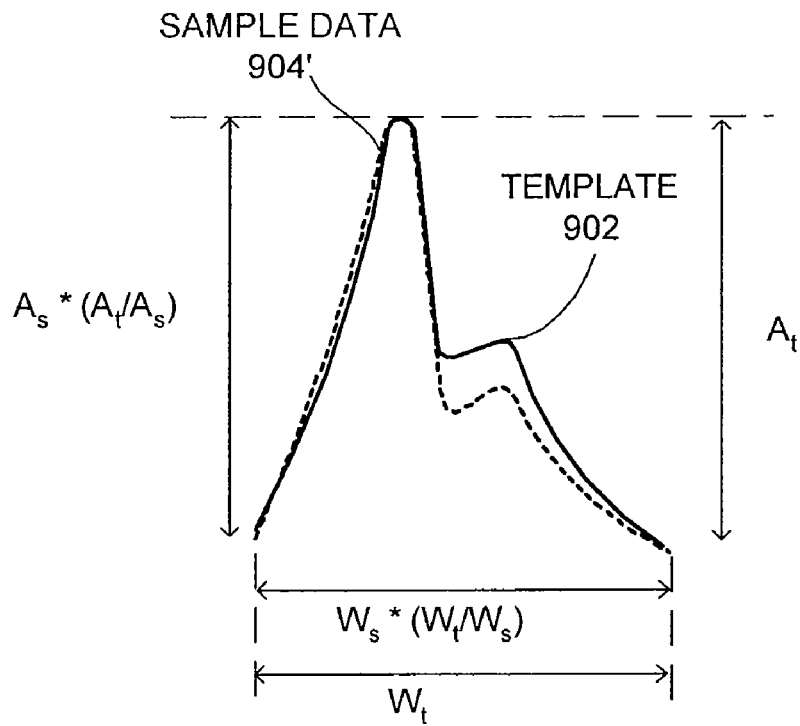

The affect of the above described normalization can be appreciated from FIGS. 9A and 9B. Referring to FIG. 9A, an exemplary PPG template 902 and exemplary PPG sample data 904 are shown, where the portion the sample data (representative of a cycle of a PPG signal) has a lower peak-to-peak amplitude and shorter width than the template. Referring now to FIG. 9B, the sample data 904 has been normalized to produce sample data 904'. It can be appreciated from these FIGS. that sample data 904' is more similar to the template 902 than sample data 904. This difference in similarity is not due to motion induced noise, but rather to other factors unrelated to motion induced noise.

Now, still referring to FIGS. 9A and 9B, and also referring back to FIGS. 1 and 2, it can be appreciated that the each cycle of the exemplary PPG signal 102 shown in FIG. 1 is relatively similar to the template 902 shown in FIGS. 9A and 9B. It can also be appreciated that the portion 208 of the exemplary PPG signal 202 shown in FIG. 2 is not similar to the template 902 shown in FIGS. 9A and 9B. This is because the PPG signal 102 shown in FIG. 1 is relatively unaffected by motion induced noise, whereas the portion 208 of the PPG signal 202 shown in FIG. 2 is highly affected by motion induced noise.

In accordance with specific embodiments, the determined level of similarity between the portion of the sensor signal and the template can be compared to one or more threshold, to classify the level of motion induced noise in the sensor signal. For example, if the determined level of similarity is compared to a single threshold, the level of motion induced noise can be classified as being either low or high. If the determined level of similarity is compared to two thresholds, the level of motion induced noise can be classified as being either low, medium or high. More thresholds can be used to classify the level of motion induced noise with more granularity. Generally, where N thresholds are used, the level of motion induced noise can be classified as one of N+1 levels. Such threshold values can be predefined or preprogrammed, or as described below they can be updated from time to time.

It is also within the scope of the present invention to use the level of similarity as a reliability index indicative of the reliability of the sensor signal. This can be done in a similar manner as was discussed above with reference to the histogram techniques for estimating a level of motion induced noise. For example, if a sensor signal is deemed to be highly reliable, then a measurement, adjustment, decision or calculation that is based on the sensor signal may be highly weighted. If a sensor signal is deemed to not be reliable, then a measurement, adjustment, decision or calculation based on the sensor signal may be lightly weighted, or disregarded. It may also be that the measurement, adjustment, decision or calculation is not made, when the sensor signal is deemed unreliable.

In a similar manner as was discussed above with regards to the histogram techniques for estimating a level of motion induced noise, the signal produced by the implantable sensor can be used by the implantable system to monitor or adjust a parameter. In such embodiments, there can be a determination, based on the estimated level of motion induced noise (or level of similarity), of whether to use the sensor signal (or more specifically, the sample data representative of the signal) to monitor or adjust a parameter, as indicated at a step 808 in FIG. 8. Also, as described above, it is also possible that a decision be made, based on the estimated level of motion induced noise, to further process (e.g., further filter) the sensor signal (or samples thereof).

Some sensor signals, such as PPG signals, sometimes experience a morphology reversal along their vertical axis. This phenomenon may occur, e.g., due to increased pressure in the vicinity of the sensor. Specific embodiments check for such morphology reversals, rather than assuming there is a high level of noise when there is a low level of similarity. In specific embodiments, the morphology is reversed, along a vertical axis, of one of the template or the portion of the sensor signal. Thereafter, a level of similarity is determined between the morphology of the portion of the sensor signal and the template (one of which have been reversed), and a level of motion induced noise is determined based on the level of similarity. This can occur each time there is a morphology comparison. More likely, to reduce processing, this occurs only when there is a determination that there is a low level of similarity between the non-reversed template and a non-reversed portion of the sensor signal. In certain embodiments, a reversed template always stored in the implantable device. Then, whenever the template is updated, as described below, the reverse template is also updated.

Figure 10A:
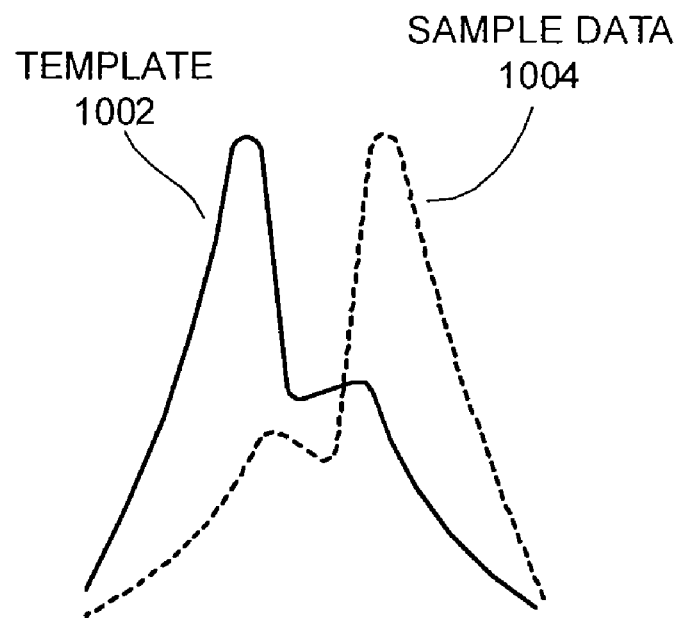
FIGS. 10A and 10B, which illustrate an exemplary portion of a PPG signal as compared to a template, are useful for describing how a sensor signal may experience a phase reversal, and how such a phase reversal can be dealt with in accordance with certain embodiments of the present invention.
Figure 10B:
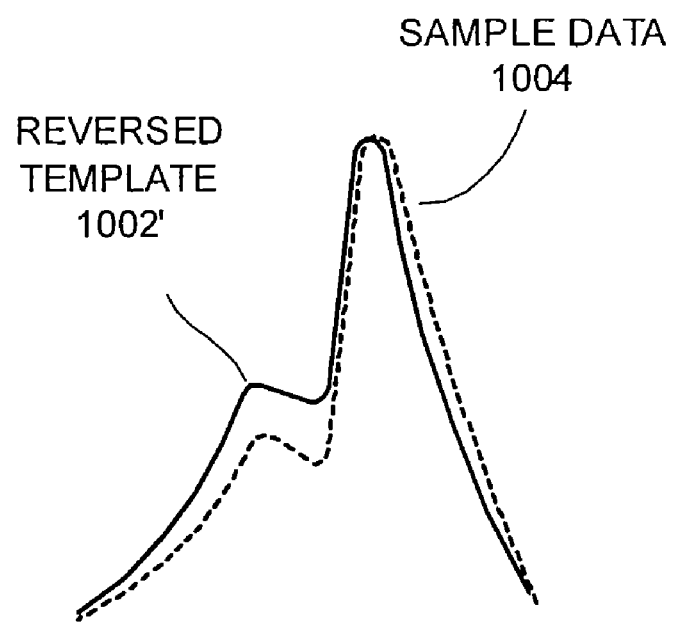

FIG. 10A illustrates an exemplary template 1002 and exemplary sample data 1004 from a PPG signal that experienced morphology reversal. FIG. 10B illustrates how there is a high level of similarity between a reverse of template 1002 (i.e., reversed template 1002') and the portion of the sensor signal represented by the sample data 1004. This level of similarity may not be recognized if the possibility of the sensor signal morphology reversing was not considered using embodiments of the present invention. Accordingly, if the reverse template was not used in the comparison, it may have been determined that the level of motion induced noise was relatively high, when it actually was not.

Since the performance of an implantable sensor may change over time due to electrical depletion of the sensor and/or the battery that powers the sensor, tissue overgrowth and/or other factors, the parameters that are used to classify the level of motion induced noise can be updated from time to time. This can include adjusting the template whose morphology is compared to the sensor signal. For example, in accordance with an embodiment, the morphology of a plurality of cycles of the sensor signal can be stored and averaged to produce a new template from time to time. Preferably, the sample data that is stored and used to produce the updated template is found to have a low level of motion induced noise. The template can be updated periodically, e.g., once a week, once a month, etc. Alternatively, the template can be updated whenever it is determined that a level of similarity between a current template and an average morphology of a plurality of cycles of the sensor signal (when noise is determined to be low) exceeds an update threshold level. Such a comparison can occur generally continuously, or periodically. For example, each time a portion of the sensor signal is determined to have a low level of noise, that portion can be used to update an average representation of the sensor signal. Each time the average is updated, a level of similarity between the average and the current template can be determined, and the level of similarity can be compared to the update threshold. Alternatively, a level of similarity between the average and the current template can take place periodically.

Exemplary Stimulation Device

Figure 11A:
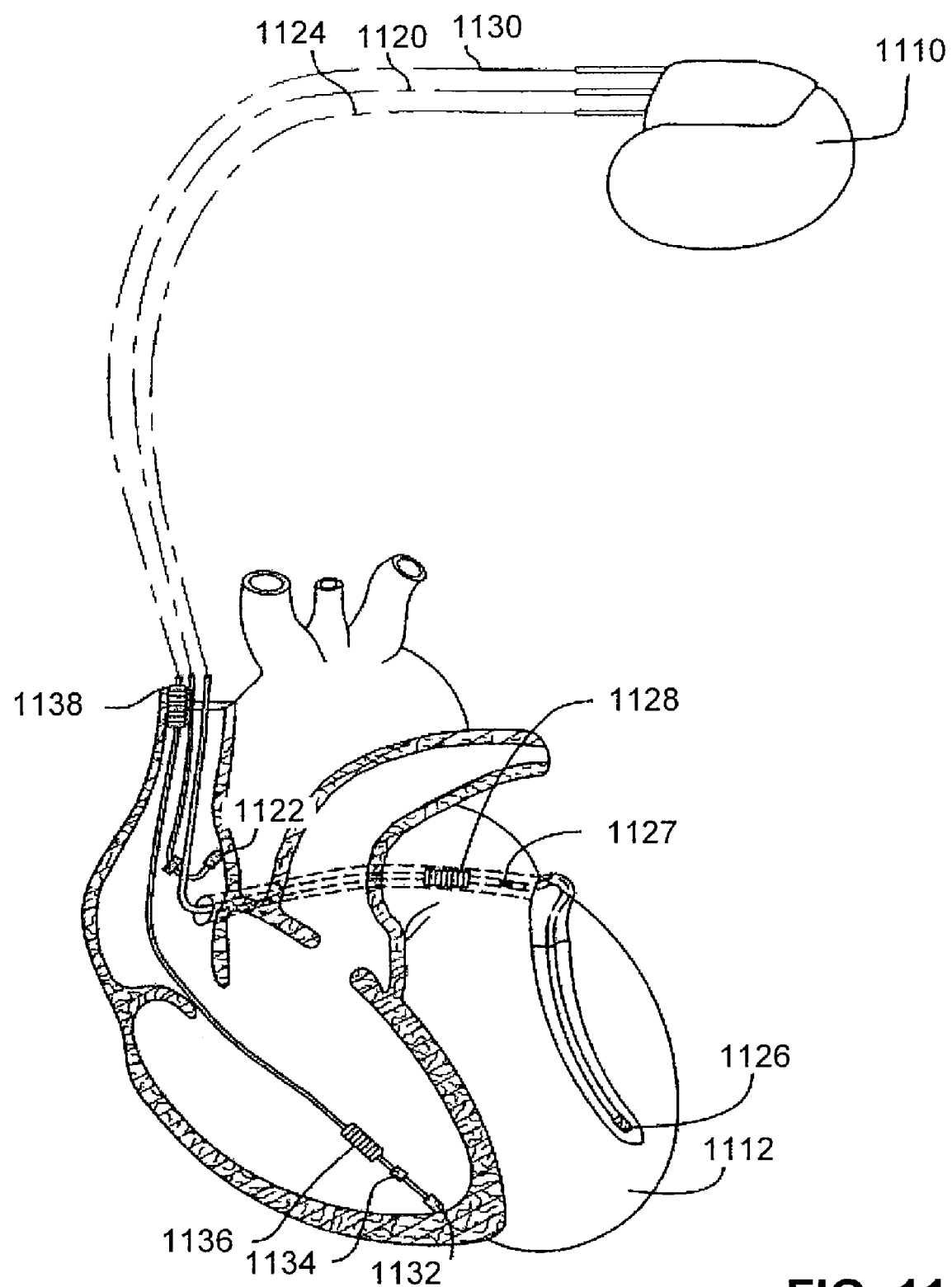
FIG. 11A illustrates an exemplary implantable stimulation device in electrical communication with a patient's heart by way of three leads, which are suitable for delivering multi-chamber stimulation and shock therapy.

Referring to FIG. 11A, an exemplary implantable stimulation device 1110 is shown as being in electrical communication with a patient's heart 1112 by way of three leads, 1120, 1124 and 1130, suitable for delivering multi-chamber stimulation and shock therapy. The various features of the various embodiments of the present invention can be implemented by an implantable device that is similar to device 1110, or by an implantable device that includes more or less functionality than device 1110.

To sense atrial cardiac signals and to provide right atrial chamber stimulation therapy, the stimulation device 1110 is coupled to an implantable right atrial lead 1120 having at least an atrial tip electrode 1122, which typically is implanted in the patient's right atrial appendage.

To sense left atrial and ventricular cardiac signals and to provide left-chamber pacing therapy, the stimulation device 1110 is coupled to a "coronary sinus" lead 1124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The exemplary coronary sinus lead 1124 is designed to receive atrial and ventricular cardiac signals and to deliver left ventricular pacing therapy using at least a left ventricular tip electrode 1126, left atrial pacing therapy using at least a left atrial ring electrode 1127, and shocking therapy using at least a left atrial coil electrode 1128.

The stimulation device 1110 is also shown in electrical communication with the patient's heart 1112 by way of an implantable right ventricular lead 1130 having, in this embodiment, a right ventricular tip electrode 1132, a right ventricular ring electrode 1134, a right ventricular (RV) coil electrode 1136, and an SVC coil electrode 1138. Typically, the right ventricular lead 1130 is transvenously inserted into the heart 1112 so as to place the right ventricular tip electrode 1132 in the right ventricular apex so that the RV coil electrode 1136 will be positioned in the right ventricle and the SVC coil electrode 1138 will be positioned in the superior vena cava. Accordingly, the right ventricular lead 1130 is capable of receiving cardiac signals and delivering stimulation in the form of pacing and shock therapy to the right ventricle.

Figure 11B:
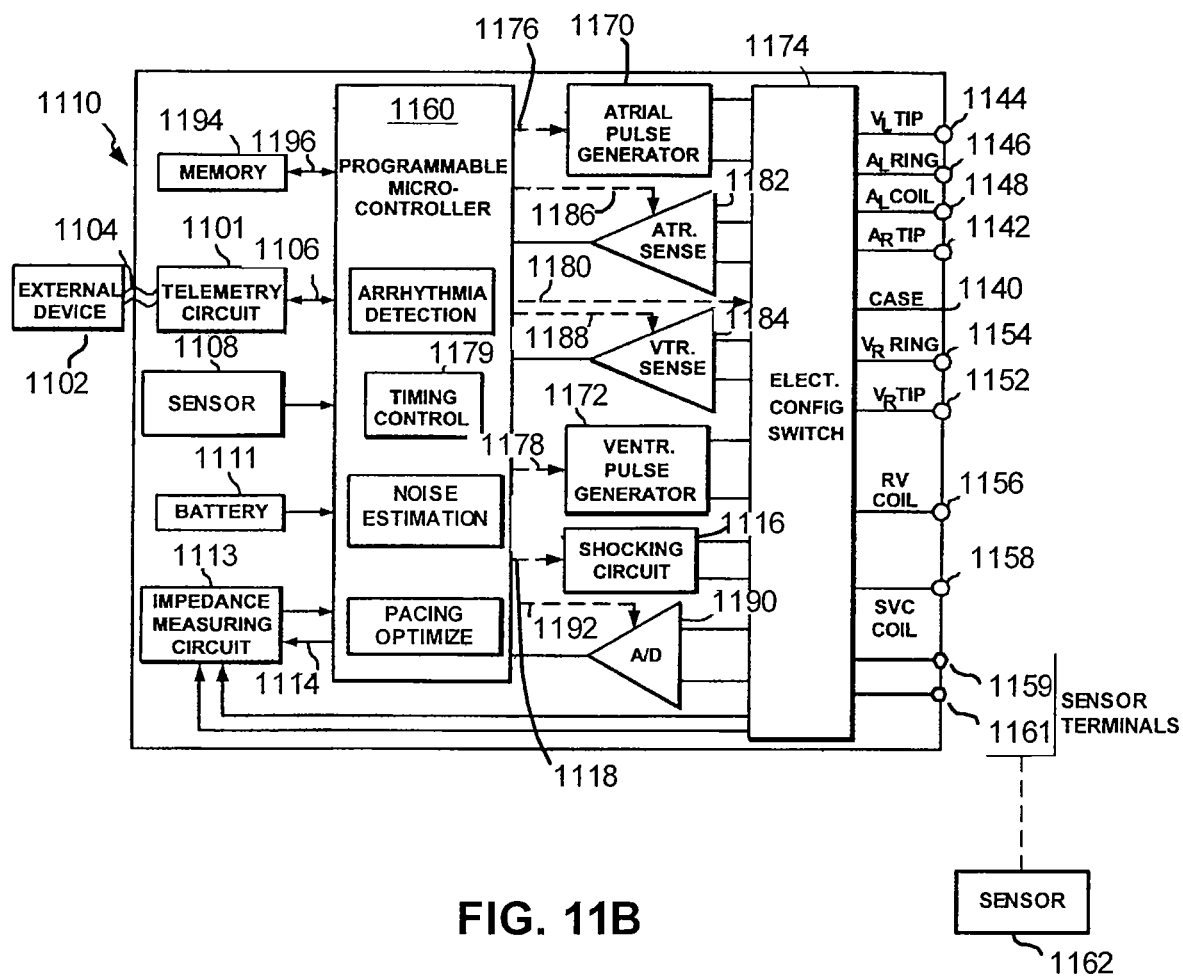
FIG. 11B is a simplified block diagram of the multi-chamber implantable stimulation device of FIG. 11A.

As illustrated in FIG. 11B, a simplified block diagram is shown of the multi-chamber implantable stimulation device 1110, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 1140 for the stimulation device 1110, shown schematically in FIG. 11B, is often referred to as the "can", "case" or "case electrode" and may be programmably selected to act as the return electrode for all "unipolar" modes. The housing 1140 may further be used as a return electrode alone or in combination with one or more of the coil electrodes, 1128, 1136 and 1138, for shocking purposes. The housing 1140 further includes a connector (not shown) having a plurality of terminals, 1142, 1144, 1146, 1148, 1152, 1154, 1156, and 1158 (shown schematically and, for convenience, the names of the electrodes to which they are connected are shown next to the terminals).

As such, to achieve right atrial sensing and pacing, the connector includes at least a right atrial tip terminal (AR TIP) 1142 adapted for connection to the atrial tip electrode 1122.

To achieve left chamber sensing, pacing and shocking, the connector includes at least a left ventricular tip terminal (VL TIP) 1144, a left atrial ring terminal (AL RING) 1146, and a left atrial shocking terminal (AL COIL) 1148, which are adapted for connection to the left ventricular tip electrode 1126, the left atrial ring electrode 1127, and the left atrial coil electrode 1128, respectively.

To support right chamber sensing, pacing and shocking, the connector further includes a right ventricular tip terminal (VR TIP) 1152, a right ventricular ring terminal (VR RING) 1154, a right ventricular shocking terminal (RV COIL) 1156, and an SVC shocking terminal (SVC COIL) 1158, which are adapted for connection to the right ventricular tip electrode 1132, right ventricular ring electrode 1134, the RV coil electrode 1136, and the SVC coil electrode 1138, respectively.

The connector is also shown as including sensor terminals 1159 and 1161 which can be configured for connection to the wires a sensor module located on or within a lead.

At the core of the stimulation device 1110 is a programmable microcontroller 1160 which controls the various modes of stimulation therapy, including pacing optimization and anti-arrhythmia therapy.

In accordance with certain embodiments, a sensor 1162 that is sensitive to motion induced noise, can be attached to the implantable device 1110 by one or more lead connected to terminals 1159 and/or 1161 to thereby provide analog sensor signals to the implantable device. Such a sensor can be attached to a lead or located within a lead. Switch 1174 can provide such signals to an analog-to-digital (A/D) converter 1190 that converts the signals to a digital format (e.g., into sample data) understood by the microcontroller 1160. It is also possible that a dedicated ND converter be provided within the implantable device 1110 for the purpose of digitizing signals received from the sensor 1162 that is sensitive to motion induced noise. If the sensor 1162 provides digital signals to the implantable device 1110, then such signals may be provided directly to the microcontroller 1110. In certain embodiments, the microcontroller performs the processing that determines the level of motion induced noise in a sensor signal. It is also possible that the implantable device 1110 include circuitry, external to the microcontroller 1160, which is dedicated to determining the level of motion induced noise in a sensor signal.

The microcontroller 1110 can also perform any preprocessing of sample data, such as, but not limited to filtering, normalizing, detrending, rectifying, and the like, examples of which are discussed above. As was described above, in certain embodiments the sample data being analyzed, to determine the level of motion induced noise in a signal, has already been high pass filtered, normalized detrended, and/or rectified.

In accordance with certain embodiments, the implantable device can include more than one sensor that is sensitive to motion induced noise.

A sensor 1108 that is sensitive to motion induced noise can be located within the housing 1140, or within a further housing (not shown) attached to the housing 1140. Where the sensor 1108 is a PPG and/or oximetry sensor, the housing containing the sensor may include one or more window to allow for light transmission/reflection, as will be understood from various applications and patents incorporated herein by reference above.

The sensor 1108 and/or 1162 can be a PPG/oximetry sensor. Alternatively, or additionally, the sensor 1108 and/or 1162 can be a glucose sensor, a pressure sensor, a temperature sensor, a microphone, impedance sensors, venous oxygen sensors, or the like. These are just a few examples of the types of sensors that may be sensitive to motion induced noise, which are not meant to limit the scope of the present invention.

In specific embodiments, the microcontroller 1160 can determine measures of blood oxygen saturation based on the signals it receives from a PPG/oximetry sensor (e.g., 1108 and/or 1162), which can be located within the housing 1140, or attached to or within a sensor lead 1159 and/or 1161. Such measures of oxygen saturation can be used, e.g., for pacing optimization, disease monitoring, and the like. Additionally or alternatively, the measures of oxygen saturation can be stored in memory 1194 for later transmission to an external device 1102 using the telemetry circuit 1101.

As is well known in the art, the microcontroller 1160 can include one or more microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 1160 includes the ability to analyze signals (data) as controlled by a program code stored in a designated block of memory. The details of the design of the microcontroller 1160 are not critical to the present invention. Rather, any suitable microcontroller 1160 can be used to carry out the functions described herein. The use of microprocessor-based control circuits for performing timing, control and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 11B, an atrial pulse generator 1170 and a ventricular pulse generator 1172 generate pacing stimulation pulses for delivery by the right atrial lead 1120, the right ventricular lead 1130, and/or the coronary sinus lead 1124 via an electrode configuration switch 1174. It is understood that in order to provide stimulation therapy in each of the four chambers of the heart, the atrial and ventricular pulse generators, 1170 and 1172, may include dedicated, independent pulse generators, multiplexed pulse generators, or shared pulse generators. The pulse generators, 1170 and 1172, are controlled by the microcontroller 1160 via appropriate control signals, 1176 and 1178, respectively, to trigger or inhibit the stimulation pulses.

The microcontroller 1160 further includes timing control circuitry 1179 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 1174 includes a plurality of switches for connecting the desired electrodes to the appropriate I/O circuits, thereby providing complete electrode programmability. Accordingly, the switch 1174, in response to a control signal 1180 from the microcontroller 1160, determines the polarity of the stimulation pulses (e.g., unipolar, bipolar, combipolar, etc.) by selectively closing the appropriate combination of switches (not shown) as is known in the art. The switch 1174 can also be used to connect wires from an oximetry sensor 802 to appropriate I/O circuits.

Atrial sensing circuits 1182 and ventricular sensing circuits 1184 may also be selectively coupled to the right atrial lead 1120, coronary sinus lead 1124, and the right ventricular lead 1130, through the switch 1174 for detecting the presence of cardiac activity in each of the four chambers of the heart. Accordingly, the atrial (ATR. SENSE) and ventricular (VTR. SENSE) sensing circuits, 1182 and 1184, may include dedicated sense amplifiers, multiplexed amplifiers, or shared amplifiers. The switch 1174 determines the "sensing polarity" of the cardiac signal by selectively closing the appropriate switches, as is also known in the art. In this way, the clinician may program the sensing polarity independent of the stimulation polarity.

Each sensing circuit, 1182 and 1184, preferably employs one or more low power, precision amplifiers with programmable gain and/or automatic gain control, bandpass filtering, and a threshold detection circuit, as known in the art, to selectively sense the cardiac signal of interest. The automatic gain control enables the device 1110 to deal effectively with the difficult problem of sensing the low amplitude signal characteristics of atrial or ventricular signals.

The outputs of the atrial and ventricular sensing circuits, 1182 and 1184, are connected to the microcontroller 1160 which, in turn, are able to trigger or inhibit the atrial and ventricular pulse generators, 1170 and 1172, respectively, in a demand fashion in response to the absence or presence of cardiac activity, in the appropriate chambers of the heart. The sensing circuits, 1182 and 1184, in turn, receive control signals over signal lines, 1186 and 1188, from the microcontroller 1160 for purposes of measuring cardiac performance at appropriate times, and for controlling the gain, threshold, polarization charge removal circuitry (not shown), and timing of any blocking circuitry (not shown) coupled to the inputs of the sensing circuits, 1182 and 1186.

For arrhythmia detection, the device 1110 utilizes the atrial and ventricular sensing circuits, 1182 and 1184, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 1160 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 1190. The data acquisition system 1190 is configured to acquire intracardiac electrogram signals, convert the raw analog data into a digital signal, and store the digital signals for later processing and/or telemetric transmission to an external device 1102. The data acquisition system 1190 is coupled to the right atrial lead 1120, the coronary sinus lead 1124, and the right ventricular lead 1130 through the switch 1174 to sample cardiac signals across any pair of desired electrodes.

The data acquisition system 1190 can be coupled to the microcontroller 1160, or other detection circuitry, for detecting an evoked response from the heart 1112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 1160 detects a depolarization signal during a window following a stimulation pulse, the presence of which indicates that capture has occurred. The microcontroller 1160 enables capture detection by triggering the ventricular pulse generator 1172 to generate a stimulation pulse, starting a capture detection window using the timing control circuitry 1179 within the microcontroller 1160, and enabling the data acquisition system 1190 via control signal 1192 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 1160 is further coupled to a memory 1194 by a suitable data/address bus 1196, wherein the programmable operating parameters used by the microcontroller 1160 can be stored and modified, as required, in order to customize the operation of the stimulation device 1110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 1112 within each respective tier of therapy.

Data acquired by the data acquisition system 1190 (and optionally stored) can be used for subsequent analysis to guide the programming of the device and/or to monitor oxygen saturation, appropriately adjust pacing interval parameters, select optimum pacing intervals, and/or select appropriate anti-arrhythmia therapy. In accordance with specific embodiments, template information can be stored in memory 1194. Additionally, threshold(s) and bin definitions can be stored in memory 1194.

The operating parameters of the implantable device 1110 may be non-invasively programmed into the memory 1194 through a telemetry circuit 1101 in telemetric communication with the external device 1102, such as a programmer, transtelephonic transceiver, or a diagnostic system analyzer. The telemetry circuit 1101 is activated by the microcontroller by a control signal 1106. The telemetry circuit 1101 advantageously allows intracardiac electrograms, oxygen saturation information and status information relating to the operation of the device 1110 (as contained in the microcontroller 1160 or memory 1194) to be sent to an external device 1102 through an established communication link 1104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, issued Aug. 14, 2001, entitled "Efficient Generation of Sensing Signals in an Implantable Medical Device such as a Pacemaker or ICD" (note: this relates to transfer of EGM data) (McClure et al.), which patents are hereby incorporated herein by reference.

The stimulation device 1110 additionally includes a battery 1111 which provides operating power to all of the circuits shown in FIG. 11B. For the stimulation device 1110, which employs shocking therapy, the battery 1111 should be capable of operating at low current drains for long periods of time, and then be capable of providing high-current pulses (for capacitor charging) when the patient requires a shock pulse. The battery 1111 should also have a predictable discharge characteristic so that elective replacement time can be detected. The battery 1111 can also power the sensor that is sensitive to motion induced noise. A separate battery may alternatively be used.

The stimulation device 1110 can further include a magnet detection circuitry (not shown), coupled to the microcontroller 1160. It is the purpose of the magnet detection circuitry to detect when a magnet is placed over the stimulation device 1110, which magnet may be used by a clinician to perform various test functions of the stimulation device 1110 and/or to signal the microcontroller 1160 that the external programmer 1102 is in place to receive or transmit data to the microcontroller 1160 through the telemetry circuits 1101.

As further shown in FIG. 11B, the device 1110 is shown as having an impedance measuring circuit 1113 which is enabled by the microcontroller 1160 via a control signal 1114. The known uses for an impedance measuring circuit 1113 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; measuring thoracic impedance for detecting and assessing the severity of pulmonary edema; detecting when the device has been implanted; measuring stroke volume; and detecting the opening of heart valves, etc. The impedance measuring circuit 1113 is advantageously coupled to the switch 1174 so that any desired electrode may be used. In addition, to facilitate the measurement of peripheral tissue edema, extra electrodes can be added to the device housing, thereby limiting the test electric field to the peripheral tissue.

In the case where the stimulation device 1110 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 1160 further controls a shocking circuit 1116 by way of a control signal 1118. The shocking circuit 1116 generates shocking pulses of low (up to 0.5 Joules), moderate (0.5-10 Joules), or high energy (11 to 40 Joules), as controlled by the microcontroller 1160. Such shocking pulses are applied to the patient's heart 1112 through at least two shocking electrodes, and as shown in this embodiment, selected from the left atrial coil electrode 1128, the RV coil electrode 1136, and/or the SVC coil electrode 1138. As noted above, the housing 1140 may act as an active electrode in combination with the RV electrode 1136, or as part of a split electrical vector using the SVC coil electrode 1138 or the left atrial coil electrode 1128 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of ventricular fibrillation. Accordingly, the microcontroller 1160 is capable of controlling the synchronous or asynchronous delivery of the shocking pulses. Another approach to electrical anti-arrhythmia therapy is anti-tachycardia pacing, in which low-voltage pacing pulses are applied to pace-terminate the arrhythmia. This approach is particularly effective in low rate ventricular tachycardias.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for estimating a level of noise in a signal produced by an implantable sensor that is sensitive to motion induced noise, the method comprising:
    (a) obtaining sample data representative of a window of the signal produced by the implantable sensor that is sensitive to motion induced noise, the sample data including a plurality of samples each having a magnitude;
    (b) assigning each of at least some of the samples to one of a plurality of bins based on the magnitude of the sample, wherein each bin corresponds to a different range of magnitudes; and
    (c) estimating a level of motion induced noise in the sensor signal based on a distribution of the samples to the bins, wherein the level of motion induced noise comprises a level of motion artifacts.

2. The method of claim 1, wherein:
step (b) comprises producing a histogram, for the window of the sensor signal, based on the plurality of samples; and
step (c) comprises estimating the level of motion induced noise in the sensor signal based on a distribution of the histogram.

3. The method of claim 1, wherein the sample data can be used by the implantable system to monitor or adjust a parameter, the method further comprising:
    (d) determining, based on the estimated level of noise, whether to use the sample data to monitor or adjust the parameter.

4. The method of claim 1, wherein the plurality of bins includes at least a low bin defining a lowest magnitude range and a high bin defining a highest magnitude range.

5. The method of claim 4, wherein step (c) includes determining a ratio of a number of samples in the highest N bins to a number of samples in the lowest M bins, or vice versa, wherein N and M are integers $\geq 1$, and N+M$\leq$a total number of the bins.

6. The method of claim 5, further comprising:
    (d) using the ratio as a reliability index indicative of reliability of the sample data.

7. The method of claim 5, wherein step (c) includes comparing the ratio to N thresholds, to estimate the level of motion induced noise in the sensor signal as being one of N+1 levels, where N is an integer that is ≧1.

8. The method of claim 1, wherein step (c) includes:
(c.i) fitting a line to the distribution;
(c.ii) determining a slope of the line fit to the distribution; and
(c.iii) estimating the level of motion induced noise based on the slope.

9. The method of claim 8, wherein step (c.iii) comprises comparing the slope of the line to N thresholds, to estimate the level of motion induced noise in the sensor signal as being one of N+1 levels, where N is an integer that is ≧1.

10. The method of claim 1, further comprising:
storing sample data that is indicative of portions of the sensor signal when the level of motion induced noise is estimated to be low; and
updating, based on the stored sample data, one or more threshold that is used to estimate the level of motion induced noise at step (c).

11. The method of claim 1, further comprising:
storing sample data that is indicative of windows of the sensor signal when the level of motion induced noise is estimated to be low; and
updating, based on the stored sample data, at least one boundary of at least one said bin.

12. In an implantable system, a method for estimating a level of noise in a signal produced by an implantable sensor that is sensitive to motion induced noise, the method comprising:
(a) obtaining sample data representative of a window of the signal produced by the implantable sensor that is sensitive to motion induced noise, the sample data including a plurality of samples each having a magnitude;
(b) assigning each of at least some of the samples to one of a plurality of bins based on the magnitude of the sample, wherein each bin corresponds to a different range of magnitudes; and
(c) estimating a level of motion induced noise in the sensor signal based on a distribution of the samples to the bins, wherein the implantable sensor is an implanted photoplethysmography (PPG) sensor, and wherein the signal that is sensitive to motion induced noise is a PPG signal.

13. In an implantable system, a method for estimating a level of noise in a signal produced by an implantable sensor that is sensitive to motion induced noise, the method comprising:
(a) obtaining sample data representative of the signal produced by the implantable sensor that is sensitive to motion induced noise;
(b) producing a histogram for a window of the sensor signal, based on the sample data; and
(c) estimating the level of motion induced noise in the sensor signal based on a distribution of the histogram, wherein the level of motion induced noise comprises a level of motion artifacts.

14. The method of claim 13, wherein the histogram produced at step (b) includes at least a low bin defining a lowest magnitude range and a high bin defining a highest magnitude range.

15. The method of claim 14, wherein step (c) includes:
determining a ratio of a number of samples in the highest N bins to a number of samples in the lowest M bins, or vice versa, wherein N and M are integers ≧1, and N+M≦5 a total number of the bins; and
estimating the level of motion induced noise based on the ratio.

16. The method of claim 14, wherein step (c) includes:
fitting a line to the distribution of the histogram;
determining a slope of the line fit to the distribution histogram; and
estimating the level of motion induced noise based on the slope.

17. An implantable system including an implantable sensor that is sensitive to motion induced noise, comprising:
means for obtaining sample data representative of a window of the signal produced by the implantable sensor that is sensitive to motion induced noise, the sample data including a plurality of samples each having a magnitude;
means for assigning each of at least some of the samples to one of a plurality of bins based on the magnitude of the sample, wherein each bin corresponds to a different range of magnitudes; and
means for estimating a level of motion induced noise in the sensor signal based on a distribution of the samples to the bins, wherein the level of motion induced noise comprises a level of motion artifacts.

18. The system of claim 17, wherein:
the means for assigning produces a histogram, for the window of the sensor signal, based on the plurality of samples; and
the means for estimating estimates the level of motion induced noise in the sensor signal based on a distribution of the histogram.

19. The system of claim 17, wherein the implantable system uses the signal produced by the implantable sensor to monitor or adjust a parameter, and where the implantable system determines, based on the estimated level of noise, whether to use the sensor signal to monitor or adjust the parameter.

20. The system of claim 17, wherein the means for estimating a level of motion induced noise:
determines a ratio of a number of samples in the highest N bins to a number of samples in the lowest M bins, or vice versa, wherein N and M are integers ≧1, and N+M≦a total number of the bins; and
estimates the level of motion induced noise based on the ratio.

21. The system of claim 17, wherein the means for estimating the level of motion induced noise:
fits a line to the distribution;
determines the slope of the line fit to the distribution; and
estimates the level of motion induced noise based on the slope.

22. The system of claim 17, wherein the implantable sensor is an implanted photoplethysmography (PPG) sensor, and wherein the signal that is sensitive to motion induced noise is a PPG signal.

* * * * *